United States Patent [19]
Elsberry et al.

[11] Patent Number: 5,603,703
[45] Date of Patent: Feb. 18, 1997

[54] SELECTIVELY ASPIRATING STYLET

[75] Inventors: Dennis D. Elsberry, New Hope; Jane L. Kohnen, Minneapolis, both of Minn.

[73] Assignee: Medtronic, Inc., Minneapolis, Minn.

[21] Appl. No.: 430,964

[22] Filed: Apr. 28, 1995

[51] Int. Cl.$^6$ ............................................. A61M 25/00
[52] U.S. Cl. ........................... 604/268; 604/274; 604/51
[58] Field of Search ................................. 604/128, 171, 604/349–350, 280–283, 323–335, 264, 268, 164–165, 32, 30, 51, 53; 128/768, 770, 763, 766

[56] References Cited

U.S. PATENT DOCUMENTS

| | | |
|---|---|---|
| 3,920,002 | 11/1975 | Dye et al. . |
| 3,976,278 | 8/1976 | Dye et al. . |
| 5,098,411 | 3/1992 | Watson et al. . |
| 5,188,594 | 2/1993 | Zilbertstein . |
| 5,396,899 | 3/1995 | Strittmatter . |

*Primary Examiner*—Randall L. Green
*Assistant Examiner*—Perry E. VanOver
*Attorney, Agent, or Firm*—Curtis D. Kinghorn; Harold R. Patton

[57] ABSTRACT

A selectively aspirating stylet assembly comprises a stylet having proximal and distal ends, the proximal end in fluid communication with a fluid supply and the distal end disposed at or near the end of a catheter, cannula or other generally tubular member that is to be inserted to a specified location within a patient's body, so as to create a fluid flow path from the fluid supply through the generally tubular member to the specified location. A valve assembly located within the fluid flow path is operable to close off a fluid column within the stylet assembly to facilitate placement of the tubular member within the body, and to control the flow of fluids within the assembly. Insertion of the tubular member into the body is accomplished by placing a portion of the stylet within the tubular member; closing the valve assembly to create a closed fluid column; inserting the stylet/tubular member assembly into the body; and then, during the withdrawal of the stylet, opening or closing the valve assembly as necessary to control the flow of fluid within the stylet/tubular member assembly to avoid substantial aspiration of body fluid and tissue.

70 Claims, 1 Drawing Sheet

SELECTIVELY ASPIRATING STYLET

BACKGROUND present invention relates generally to selectively aspirating styler assemblies; and particularly relates to such stylet assemblies having selectively controllable flow paths such as may be used, for example, to optimally facilitate the introduction of a catheter, shunt or cannula into a parenchymatous organ or structure. The present invention also has application in connection with other procedures, such as the placement of a cannula within the body for locating a wire lead or electrode, or otherwise establishing a fluid flow path or placing an elongated tubular member between first and second locations outside and within the body, respectively.

The stylet assembly of the present invention defines a fluid flow path, allowing pressure at the inserted distal end of the stylet to be controlled to permit regulation of aspiration of tissue or fluid into the catheter or shunt during withdrawal of the stylet. As an example, one primary application of this invention involves intracerebral ventricular (ICV) catheter placement. Establishing a fluid flow path through the stylet and avoiding aspiration of tissue into the catheter requires a mechanism to prevent the creation of a vacuum while withdrawing the stylet from the catheter. However, the present invention also may be used under circumstances in which some aspiration is desired, as in the case of a biopsy from a localized area.

Insertion of a catheter, shunt or cannula into the body is often accomplished with the use of a solid stylet or guidewire which extends into the catheter to provide sufficient rigidity to facilitate passage along a desired path through body tissue. Once the catheter or shunt is properly positioned, and possibly during the positioning procedure itself, the stylet must be withdrawn. Pulling a solid stylet from a positioned catheter or shunt device creates a vacuum at the inserted open end of the device. Fluid or tissue or both is drawn into the catheter to fill the vacuum, and the displacement of the tissue may cause undesirable physiologic side effects. In the case of an ICV catheter placement, such a vacuum could result in aspiration of choroid plexus into the catheter, resulting in extreme tissue damage proximate the catheter.

Hollow stylets have been known previously. For example, U.S. Pat. No. 5,098,411 issued to Watson, discloses a hollow stylet. Such hollow stylets offer an advantage over solid ones in that they allow fluid to exit. Hollow stylets may thus be utilized to determine, through fluid return, when a desired location in the brain or other organ is reached. A specific problem during catheter placement, however, is that tissue can be "cored" in the distal opening if an open-ended hollow catheter/stylet or cannula/stylet assembly is used, and tissue can intrude through apertures in the catheter even if the assembly is not open-ended. Additionally, hollow catheter/stylet and cannula/stylet assemblies, although solid, may not have optimal rigidity, making placement within the body difficult.

Accordingly, the present invention provides new methods and apparatus for overcoming one or more of these deficiencies by providing a stylet defining a flow path which may be selectively opened or closed to optimize the rigidity of the stylet while minimizing tissue damage proximate an outer tubular member placed through use of the stylet.

SUMMARY OF THE INVENTION

As explained in more detail below, the present invention overcomes the above-noted and other shortcomings of prior stylet devices used during placement of catheters, shunts or cannula. For simplicity of expression, the invention will be described in terms of placing a catheter, and the Figures will be referred to in terms of defining a catheter. It should be clearly understood that the description is equally applicable to placing a shunt or cannula for guiding an electric lead; and that FIG. 1 is generic to such other structures. The invention is operable to provide a closed fluid column to facilitate placement of the stylet/catheter assembly into a specific selected location within the body. The closed fluid column is generally non-compressible. Such fluid column may be analogized to the fluid column obtained by crimping the top end of a fluid-filled soda straw.

An appropriate valve is used to close off the fluid column near the top end of the stylet. Although the valve need not be placed immediately on top of the stylet, it is preferable that the valve be placed in material which is generally rigid, and that the valve be placed as close as possible to the actual top of the stylet to avoid excess fluid volumes and to avoid use of any members which might change in volume, thereby forcing fluid out and destroying the fluid column.

Preferably, the valve will be a rotary valve such as a stop-cock valve as used in intravenous delivery systems. However, a poppet or other longitudinally shifting type of valve may also be satisfactory. The important consideration is that the valve used not displace fluid during an operation; accordingly, a stop-cock valve having a rotary motion, or a poppet valve having a transverse motion relative to the fluid passageway, is currently believed to be most appropriate.

The fluid column may be established by pumping a selected fluid through a catheter/stylet assembly against some resistance (e.g. the use of a hypodermic syringe into a small vial of similar fluid), so as to provide an air-free column of fluid within the catheter/stylet assembly. The valve may then be closed to isolate the column. Tissue in the path of the stylet/catheter assembly is parted during insertion of the assembly into the brain or other organ. Fluid may be obtained through the hollow stylet and may be monitored to determine when a desired location is reached. Additionally, the valve may be opened, and pressures equalized, after insertion of the catheter/stylet assembly to place the end of the catheter at the desired location. Fluid can be infused down the lumen of the stylet, filling the space created by any withdrawal of the stylet. Using replacement fluid rather than drawing fluid from the distal locale may prevent harmful side effects caused by either displacing the fluid, and/or tissue damage near the tip of the device caused by a vacuum. Once the desired location is reached, the hollow stylet is to be completely removed, leaving only the flexible catheter in the brain or other organ.

Examples of the more important features of this invention have been broadly outlined in order that the detailed description that follows may be better understood and so that contributions which this invention provides to the art may be better appreciated. There are, of course, additional features of the invention which will be described herein and which will be included within the subject matter of the claims appended hereto.

DETAILED DESCRIPTION OF THE INVENTION

Figure 1:
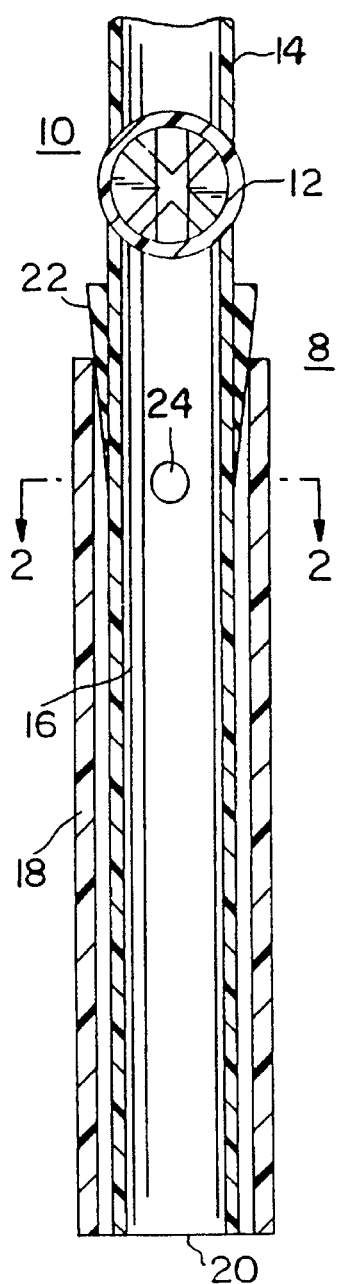
FIG. 1 is an illustration of an open tip configuration of an exemplary hollow stylet/tubular member assembly in accordance with the present invention, depicted in vertical section, and partially in schematic representation.
Figure 2:
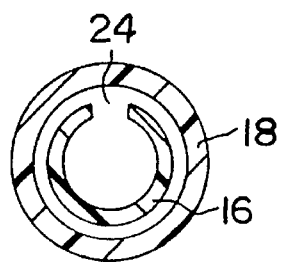
FIG. 2 is an illustration of the hollow stylet/tubular member assembly shown in FIG. 1, depicted in a cross-sectional view taken along the line 2—2 in FIG. 1.

As noted previously, the depicted tubular member/stylet assembly 8 in accordance with the present invention is shown in FIG. 1, and will be described in terms of a catheter/stylet assembly. A stylet 10 generally comprises a valve assembly 12 operatively coupled between an upper stylet body portion 14 and a lower stylet body portion 16. Both the upper and lower stylet body portions 14, 16 are hollow, rigid tubular members. The lower stylet body portion 16 is adapted for placement within catheter 18. The inner diameter of catheter 18 typically will be on the order of 0.025 inches, so that the outer diameter of the lower stylet body portion 16 generally will be approximately 0.020 inches. The inner diameter of the lower stylet body portion 16 typically will measure about 0.010 to 0.016 inches. The dimensions of the upper stylet body portion 14 generally may be about the same as the dimensions of the lower stylet body portion or larger, but it is desirable to minimize its mass. Of course, devices of other sizes are within the scope of the present invention.

The valve assembly 12 is able to provide selective fluid communication from one side of the valve to the other. Preferably, valve assembly 12 is a rotary valve such as a stop cock valve of the type typically used in intervenous delivery systems. However, as noted above, a poppet valve or another type of valve may be used, provided that the valve does not displace fluid, or displaces only a minimal volume of fluid, beneath the valve during operation. Suitable stop cock valves for use in connection with the present invention are widely available from numerous commercial suppliers. One such supplier is Burron Medical, Inc.

The upper stylet body portion 14 has two ends, the first end connected to a first side of a valve assembly 12 and the second end connected to a fluid supply. The lower stylet body portion 16 also has two ends, the first end connected to a second side of valve assembly 12 and the second end distally located away from the valve assembly and at or near the tip 20 of the catheter/stylet assembly.

Figure 3:
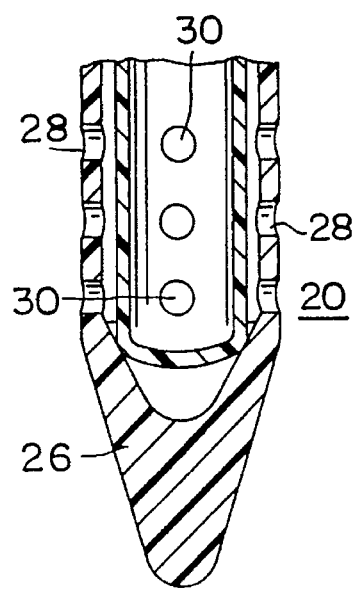
FIG. 3 is an illustration of a closed tip configuration for a hollow stylet/catheter assembly in accordance with the present invention, depicted in vertical section.

The tip 20 of the catheter/stylet assembly may be of an open tip configuration, as shown in FIG. 1, or may be of a closed tip configuration, as shown in FIG. 3. Selection of either an open tip or closed tip catheter/stylet assembly for a particular patient will depend in each case upon the circumstances surrounding the treatment to be performed. Generally, however, an open tip catheter/stylet assembly will be used when the infusion target is not to be invaded, while a closed tip configuration is preferred if the infusion target requires invasion for optimal perfusion.

Figure 4:
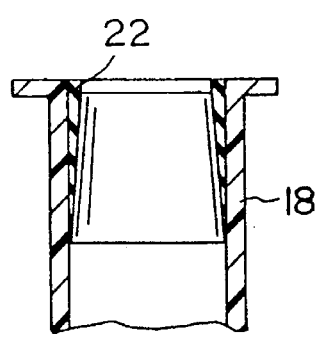
FIG. 4 is an illustration of a configuration of an exemplary upper end of a generally tubular member adapted with a sealing means in accordance with the present invention, depicted in vertical section.

As shown in FIG. 1, the lower stylet body portion 16 is configured to be placed within catheter 18. A sealing means 22 preferably is used to prevent unwanted escape of fluid from around the stylet at the upper end of the catheter. Sealing means 22 preferably comprises a silicone rubber material placed so as to fill and close the annular space between the inside diameter surface of catheter 18 and the outside diameter surface of the first end of lower stylet body portion 16. As shown in FIG. 4, the upper end of catheter 18 may be adapted with the sealing means 22. Alternatively, the lower stylet body portion 16 may be adapted with sealing means 22 (see FIG. 1), or the sealing means 22 may be separate from both lower stylet body portion 16 and catheter 18 and independently placed so as to fill and close the annular space between catheter 18 and lower stylet portion 16.

Sealing means 22 can be of a variety of shapes and sizes. As shown in FIG. 1, sealing means 22 is tapered, with the sealing material nearest valve assembly 12 being relatively thick as compared to the sealing material located away from valve assembly 12. However, the present invention is not so limited. The shape of the sealing means may vary, for example, with the size and shape of the stylet and catheter being used. That is, where either the stylet or catheter is tapered along the area to be sealed, a sealing means 22 having uniform thickness may be satisfactory. Again, the important consideration is that the sealing means 22 prevent unwanted escape of fluid from around the stylet at the upper end of the catheter.

The lower stylet body portion 16 is adapted with a backfill opening 24 located between the valve assembly 12 and the second or lower end of lower stylet body portion 16. The backfill opening 24 allows fluid to flow from within the stylet to fill the annular space between the catheter and the stylet. Such flow is necessary in creating an air-free fluid column within the catheter/stylet assembly.

As noted above, placement of the stylet within the catheter provides a more rigid assembly for passage along a desired path through body tissue. Introducing a fluid column within both the stylet and catheter makes each more rigid. Thus, allowing fluid to flow from within the stylet to fill the annular space between the catheter and the stylet provides additional rigidity to the catheter/stylet assembly. Accordingly, ease of placement is further enhanced.

In a catheter/stylet assembly having a closed tip configuration, the distal, second end of lower stylet body portion 16 is closed off and generally rounded to prevent its damaging the closed tip 26 of catheter 18. However, the sides of both catheter 18 and lower stylet body portion 16 will have at their lower ends a plurality of holes 28, 30 that permit the passage of fluid. Preferably, both the catheter and stylet are configured with four groups of three longitudinally spaced side holes equally spaced around its circumference, although the side holes 28 of the catheter and side holes 30 of the stylet need not be aligned. The exact number and placement of the holes may vary depending on the particular application.

Selective aspiration of organ tissue is achieved as follows: The lower stylet body portion 16 is placed within catheter 18 so that the space between the first end of lower stylet body portion 16 and the upper end of catheter 18 is sealed, and the second end of lower stylet body portion 16 is located within catheter 18 at or near tip 20. Valve assembly 12 is opened to permit a supply of fluid under pressure to flow through upper stylet body portion 14 and through valve assembly 12 to fill completely both catheter 18 and lower stylet body portion 16. As noted above, establishing fluid columns within the catheter and stylet may be accomplished by pumping a selected fluid through the catheter/stylet assembly against some resistance, e.g. using a hypodermic syringe in a vial of fluid to provide an air-free column of fluid within the catheter/stylet assembly. Once catheter 18 and lower stylet body portion 16 are filled with fluid, valve assembly 12 is closed to prevent any fluid communication between the upper and lower stylet body portion 14, 16. At this point, the catheter/stylet assembly may be inserted to a desired location within the patient's body in a conventional manner. Then, valve assembly 12 is opened or closed as necessary so that the desired selective aspiration is obtained.

Although the preferred embodiment of this invention has been described hereinabove in some detail, it should be appreciated that a variety of embodiments will be readily available to persons utilizing the invention for a specific end use. The description of the apparatus and method of this invention is not intended to be limiting on this invention, but is merely illustrative of the preferred embodiment of this invention. Other apparatus and methods which incorporate modifications or changes to that which has been described herein are equally included within this application. Additional objects, features and advantages of the present invention will become apparent by referring to the above description of the invention in connection with the accompanying drawings.

What is claimed is:

1. A selectively aspirating stylet for use in placing a generally tubular member in a patient's body, said generally tubular member having an inside diameter surface and an upper end, said stylet comprising:

a stylet body having a lower hollow portion configured to be placed within said generally tubular member and an upper hollow portion configured to extend outside said generally tubular member, said lower hollow portion having a first end and a second end and an outside diameter surface;

a valve assembly coupled to said upper and lower portions of said stylet body to provide selective fluid communication from said upper portion through said valve to said lower portion, said valve assembly coupled to said lower portion of said stylet body at said first end of said stylet body; and sealing means placed between said inside diameter surface of said generally tubular member and said stylet body to prevent unwanted escape of fluid between said stylet body and said generally tubular member when said stylet body is placed within said generally tubular member.

2. A selectively aspirating stylet for use in placing a catheter in a patient's body, said catheter having an inside diameter surface and an upper end, said stylet comprising:

a stylet body having a lower hollow portion configured to be placed within said catheter and an upper hollow portion configured to extend outside said catheter, said lower hollow portion having a first end and a second end and an outside diameter surface;

a valve assembly coupled to said upper and lower portions of said stylet body to provide selective fluid communication from said upper portion through said valve to said lower portion, said valve assembly coupled to said lower portion of said stylet body at said first end of said stylet body; and sealing means placed between said inside diameter surface of said catheter and said stylet body to prevent unwanted escape of fluid between said stylet body and said catheter when said stylet body is placed within said catheter.

3. The selectively aspirating stylet of claim 2 wherein the ultimate end of said second end of said lower hollow portion is generally rounded.

4. The selectively aspirating stylet of claim 2 further comprising a fluid column between said stylet body and said catheter.

5. The selectively aspirating stylet of claim 2 wherein said lower hollow portion of said stylet body has a backfill opening located between said first end and said second end of said stylet body, said backfill opening to allow fluid to flow from within said stylet body to fill the annular space between said inside diameter surface of said catheter and said outside diameter surface of said stylet body.

6. The selectively aspirating stylet of claim 2 wherein said second end of said lower hollow portion terminates in an open configuration.

7. The selectively aspirating stylet of claim 2 wherein said second end of said lower hollow portion terminates in a generally closed configuration and wherein said second end of said lower hollow portion includes at least one hole to permit the passage of fluid into and out of said lower hollow portion.

8. The selectively aspirating stylet of claim 2 wherein said sealing means comprises an elastomeric material placed around said lower hollow portion of said stylet body to fill and close the annular space between said inside diameter surface of said catheter and said outside diameter surface of said lower hollow portion of said stylet body when said lower hollow portion is placed in said catheter.

9. The selectively aspirating stylet of claim 8 wherein said sealing means is tapered, with the material of said sealing means nearest said first end of said lower hollow portion being relatively thick as compared to the material of said sealing means located nearest said second end of said lower hollow portion.

10. The selectively aspirating stylet of claim 2 wherein said sealing means comprises means placed on said upper end of said inside diameter surface of said catheter.

11. The selectively aspirating stylet of claim 10 wherein said sealing means is tapered, with the material of said sealing means nearest said upper end of said catheter being relatively thick as compared to the material of said sealing means located away from said upper end of said catheter.

12. The selectively aspirating stylet of claim 2 wherein said sealing means comprises means independently placed between said lower hollow portion of said stylet body and said upper end of said inside diameter surface of said catheter to fill and close the annular space between said stylet body and said catheter.

13. The selectively aspirating stylet of claim 12 wherein said sealing means is tapered, with the material of said sealing means at one end of said sealing means being relatively thick as compared to the material of said sealing means at an opposite end of said sealing means.

14. The selectively aspirating stylet of claim 2 wherein sealing means comprises said outer diameter surface of said lower hollow portion being tapered at said first end of said stylet body with decreasing outer diameter moving toward said second end of said stylet body, said tapered portion of said stylet body configured to contact said upper end of said inner diameter surface of said catheter and thereby prevent unwanted escape of fluid from around said stylet body at said upper end of said catheter.

15. The selectively aspirating stylet of claim 1 wherein said sealing means comprises an elastomeric material placed around said lower hollow portion of said stylet body to fill and close the annular space between said inside diameter surface of said generally tubular member and said outside diameter surface of said lower hollow portion of said stylet body when said lower hollow portion is placed in said generally tubular member.

16. The selectively aspirating stylet of claim 15 wherein said sealing means is tapered, with the material of said sealing means nearest said first end of said lower hollow portion being relatively thick as compared to the material of said sealing means located nearest said second end of said lower hollow portion.

17. The selectively aspirating stylet of claim 1 wherein said sealing means comprises means placed on said upper end of said inside diameter surface of said generally tubular member.

18. The selectively aspirating stylet of claim 17 wherein said sealing means is tapered, with the material of said sealing means nearest said upper end of said generally tubular member being relatively thick as compared to the material of said sealing means located away from said upper end of said generally tubular member.

19. The selectively aspirating stylet of claim 1 wherein said sealing means comprises means independently placed between said lower hollow portion of said stylet body and said upper end of said inside diameter surface of said generally tubular member to fill and close the annular space between said stylet body and said generally tubular member.

20. The selectively aspirating stylet of claim 19 wherein said sealing means is tapered, with the material of said sealing means at one end of said sealing means being relatively thick as compared to the material of said sealing means at an opposite end of said sealing means.

21. The selectively aspirating stylet of claim 1 wherein sealing means comprises said outer diameter surface of said lower hollow portion being tapered at said first end of said stylet body with decreasing outer diameter moving toward said second end of said stylet body, said tapered portion of said stylet body configured to contact said upper end of said inner diameter surface of said generally tubular member and thereby prevent unwanted escape of fluid from around said stylet body at said upper end of said generally tubular member.

22. The selectively aspirating stylet of claim 1 wherein said lower hollow portion of said stylet body has a backfill opening located between said first end and said second end of said stylet body, said backfill opening to allow fluid to flow from within said stylet body to fill the annular space between said inside diameter surface of said generally tubular member and said outside diameter surface of said stylet body.

23. The selectively aspirating stylet of claim 1 wherein said second end of said lower hollow portion terminates in an open configuration.

24. The selectively aspirating stylet of claim 1 wherein said second end of said lower hollow portion terminates in a generally closed configuration and wherein said second end of said lower hollow portion includes at least one hole to permit the passage of fluid into and out of said lower hollow portion.

25. The selectively aspirating stylet of claim 1 wherein the ultimate end of said second end of said lower hollow portion is generally rounded.

26. The selectively aspirating stylet of claim 1 further comprising a fluid column between said stylet body and said generally tubular member.

27. A method for placing a generally tubular member in tissue with only selective aspiration of said tissue, comprising the steps of:

providing a generally tubular member and a stylet assembly, said stylet assembly having a hollow portion extending into said generally tubular member, said stylet assembly also comprising a valve assembly providing selective fluid communication from a first side of said valve assembly to said hollow portion of said stylet assembly coupled to a second side of said valve assembly;

filling said stylet assembly and said generally tubular member with a fluid;

closing said valve assembly to prevent fluid communication between said first and second sides of said valve assembly;

inserting said generally tubular member and said hollow portion of said stylet assembly into said tissue; and withdrawing said stylet assembly from said generally tubular member in coordination with opening said valve assembly to provide selective aspiration of said tissue or fluid.

28. The method of claim 27, wherein said step of withdrawing said stylet assembly from said generally tubular member in coordination with opening said valve assembly to provide selective aspiration of said tissue is performed through opening said valve assembly prior to withdrawal of said stylet assembly from said generally tubular member to avoid substantial aspiration of said tissue as said stylet assembly is withdrawn from the generally tubular member.

29. A method for placing a catheter in tissue with only selective aspiration of said tissue, comprising the steps of:

providing a catheter and a stylet assembly, said stylet assembly having a hollow portion extending into said catheter, said stylet assembly also comprising a valve assembly providing selective fluid communication from a first side of said valve assembly to said hollow portion of said stylet assembly coupled to a second side of said valve assembly;

filling said stylet assembly and said catheter with a fluid;

closing said valve assembly to prevent fluid communication between said first and second sides of said valve assembly;

inserting said catheter and said hollow portion of said stylet assembly into said tissue; and withdrawing said stylet assembly from said catheter in coordination with opening said valve assembly to provide selective aspiration of said tissue.

30. The method of claim 29, wherein said step of withdrawing said stylet assembly from said catheter in coordination with opening said valve assembly to provide selective aspiration of said tissue is performed through opening said valve assembly prior to withdrawal of said stylet assembly from said catheter to avoid substantial aspiration of said tissue as said stylet assembly is withdrawn from the catheter.

31. A method of establishing a path between a first location outside a body and a second location within a body, comprising the steps of:

providing outside the body an elongated tubular outer member having first and second ends;

placing within the outer member at least a portion of an elongated tubular inner member,
said inner member having first and second ends,
said second end of said inner member being placed near the second end of the outer member,
said portion of said inner member placed within said outer member being proximate to said second end of said inner member,
said tubular inner member operatively coupled at the first end of said inner member to a valve assembly outside said tubular outer member, said
valve assembly operable to control the rate of flow of fluids within said inner member;

filling said inner member with a fluid;

inserting within the body the second end of the outer member and the second end of the filled inner member; and withdrawing said inner member from within said outer member.

32. The method of claim 31, wherein said second end of said inner member is placed within said outer member.

33. The method of claim 31, wherein during the withdrawal of said inner member some fluid within the inner member flows toward the second end of the inner member.

34. The method of claim 31, wherein during the withdrawal of said inner member some fluid within the inner member does not flow relative to the outer member.

35. The method of claim 31, wherein during the withdrawal of said inner member some fluid within the inner member flows relative to the outer member in a direction opposite to the direction of travel of the inner member.

36. The method of claim 31, wherein during the withdrawal of said inner member some fluid within the inner member flows relative to both the inner member and the outer member in the same direction as the direction of travel of the inner member.

37. A method for placing a generally tubular member in tissue with only selective aspiration of said tissue, comprising the steps of:

providing a generally tubular member and a stylet assembly, said stylet assembly having a hollow portion extending into said generally tubular member, said stylet assembly also comprising a valve assembly providing selective fluid communication from a first side of said valve assembly to said hollow portion of said stylet assembly coupled to a second side of said valve assembly;

filling said stylet assembly and said generally tubular member with a fluid;

closing said valve assembly to prevent fluid communication between said first and second sides of said valve assembly; and inserting said generally tubular member and said hollow portion of said stylet assembly into said tissue.

38. A method for placing a catheter in tissue with only selective aspiration of said tissue, comprising the steps of:

providing a catheter and a stylet assembly, said stylet assembly having a hollow portion extending into said catheter, said stylet assembly also comprising a valve assembly providing selective fluid communication from a first side of said valve assembly to said hollow portion of said stylet assembly coupled to a second side of said valve assembly;

filling said stylet assembly and said catheter with a fluid;

closing said valve assembly to prevent fluid communication between said first and second sides of said valve assembly; and inserting said catheter and said hollow portion of said styler assembly into said tissue.

39. A method of placing an elongated tubular member along a path between a first location outside a body and a second location within a body, comprising the steps of:

providing outside the body an elongated tubular outer member having first and second ends;

placing within the outer member at least a portion of an elongated tubular inner member, said inner member having first and second ends, said second end of said inner member being placed near the second end of the outer member, said portion of said inner member placed within said outer member being proximate to said second end of said inner member, said tubular inner member operatively coupled at the first end of said inner member to a valve assembly outside said tubular outer member, said valve assembly operable to control the rate of flow of fluids within said inner member;

filling said inner member with a fluid; and inserting within the body the second end of the outer member and the second end of the filled inner member.

40. The method of claim 39, wherein said second end of said inner member is placed within said outer member.

41. The method of claim 39, wherein during the withdrawal of said inner member some fluid within the inner member flows toward the second end of the inner member.

42. The method of claim 39, wherein during the withdrawal of said inner member some fluid within the inner member does not flow relative to the outer member.

43. The method of claim 39, wherein during the withdrawal of said inner member some fluid within the inner member flows relative to the outer member in a direction opposite to the direction of travel of the inner member.

44. The method of claim 39, wherein during the withdrawal of said inner member some fluid within the inner member flows relative to both the inner member and the outer member in the same direction as the direction of travel of the inner member.

45. A system for placing a generally tubular member in a patient's body, said system comprising:

a generally tubular member having an inside diameter surface and an upper end, a stylet body having a lower hollow portion placed within said generally tubular member and an upper hollow portion configured to extend outside said generally tubular member, said lower hollow portion having a first end and a second end and an outside diameter surface;

a valve assembly coupled to said upper and lower portions of said stylet body to provide selective fluid communication from said upper portion through said valve to said lower portion, said valve assembly coupled to said lower portion of said stylet body at said first end of said stylet body; and a fluid column between said lower hollow portion of said stylet body and said inside diameter of said generally tubular member;

whereby, said fluid column adds rigidity to said system while moving said generally tubular member into a patient's body.

46. The system of claim 45 further comprising sealing means placed between said inside diameter surface of said generally tubular member and said stylet body to prevent unwanted escape of fluid between said stylet body and said generally tubular member when said stylet body is placed within said generally tubular member.

47. The system of claim 46 wherein said sealing means comprises an elastomeric material placed around said lower hollow portion of said stylet body to fill and close the annular space between said inside diameter surface of said generally tubular member and said outside diameter surface of said lower hollow portion of said stylet body when said lower hollow portion is placed in said generally tubular member.

48. The system of claim 47 wherein said sealing means is tapered, with the material of said sealing means nearest said first end of said lower hollow portion being relatively thick as compared to the material of said sealing means located nearest said second end of said lower hollow portion.

49. The system of claim 46 wherein said sealing means comprises means placed on said upper end of said inside diameter surface of said generally tubular member.

50. The system of claim 49 wherein said sealing means is tapered, with the material of said sealing means nearest said upper end of said generally tubular member being relatively thick as compared to the material of said sealing means located away from said upper end of said generally tubular member.

51. The system of claim 46 wherein said sealing means comprises means independently placed between said lower hollow portion of said stylet body and said upper end of said inside diameter surface of said generally tubular member to fill and close the annular space between said stylet body and said generally tubular member.

52. The system of claim 51 wherein said sealing means is tapered, with the material of said sealing means at one end of said sealing means being relatively thick as compared to the material of said sealing means at an opposite end of said sealing means.

53. The system of claim 46 wherein sealing means comprises said outer diameter surface of said lower hollow portion being tapered at said first end of said stylet body with decreasing outer diameter moving toward said second end of said stylet body, said tapered portion of said stylet body configured to contact said upper end of said inner diameter surface of said generally tubular member and thereby prevent unwanted escape of fluid from around said stylet body at said upper end of said generally tubular member.

54. The system of claim 45 wherein said lower hollow portion of said stylet body has a backfill opening located between said first end and said second end of said stylet body, said backfill opening to allow fluid to flow from within said stylet body to fill the annular space between said inside diameter surface of said generally tubular member and said outside diameter surface of said stylet body.

55. The system of claim 45 wherein said second end of said lower hollow portion terminates in an open configuration.

56. The system of claim 45 wherein said second end of said lower hollow portion terminates in a generally closed configuration and wherein said second end of said lower hollow portion includes at least one hole to permit the passage of fluid into and out of said lower hollow portion.

57. The system of claim 45 wherein the ultimate end of said second end of said lower hollow portion is generally rounded.

58. A system for placing a catheter in a patient's body, said system comprising:
- a catheter having an inside diameter surface and an upper end,
- a stylet body having a lower hollow portion placed within said catheter and an upper hollow portion configured to extend outside said catheter, said lower hollow portion having a first end and a second end and an outside diameter surface; and
- a valve assembly coupled to said upper and lower portions of said stylet body to provide selective fluid communication from said upper portion through said valve to said lower portion, said valve assembly coupled to said lower portion of said stylet body at said first end of said stylet body; and
- a fluid column between said lower hollow portion of said stylet body and said inside diameter of said catheter;

whereby, said fluid column adds rigidity to said system while moving said catheter into a patient's body.

59. The system of claim 58 further comprising sealing means placed between said inside diameter surface of said catheter and said stylet body to prevent unwanted escape of fluid between said stylet body and said catheter when said stylet body is placed within said catheter.

60. The system of claim 59 wherein said sealing means comprises an elastomeric material placed around said lower hollow portion of said stylet body to fill and close the annular space between said inside diameter surface of said catheter and said outside diameter surface of said lower hollow portion of said stylet body when said lower hollow portion is placed in said catheter.

61. The system of claim 60 wherein said sealing means is tapered, with the material of said sealing means nearest said first end of said lower hollow portion being relatively thick as compared to the material of said sealing means located nearest said second end of said lower hollow portion.

62. The system of claim 59 wherein said sealing means comprises means placed on said upper end of said inside diameter surface of said catheter.

63. The system of claim 62 wherein said sealing means is tapered, with the material of said sealing means nearest said upper end of said catheter being relatively thick as compared to the material of said sealing means located away from said upper end of said catheter.

64. The system of claim 59 wherein said sealing means comprises means independently placed between said lower hollow portion of said stylet body and said upper end of said inside diameter surface of said catheter to fill and close the annular space between said stylet body and said catheter.

65. The system of claim 64 wherein said sealing means is tapered, with the material of said sealing means at one end of said sealing means being relatively thick as compared to the material of said sealing means at an opposite end of said sealing means.

66. The system of claim 59 wherein sealing means comprises said outer diameter surface of said lower hollow portion being tapered at said first end of said stylet body with decreasing outer diameter moving toward said second end of said stylet body, said tapered portion of said stylet body configured to contact said upper end of said inner diameter surface of said catheter and thereby prevent unwanted escape of fluid from around said stylet body at said upper end of said catheter.

67. The system of claim 58 wherein said lower hollow portion of said stylet body has a backfill opening located between said first end and said second end of said stylet body, said backfill opening to allow fluid to flow from within said stylet body to fill the annular space between said inside diameter surface of said catheter and said outside diameter surface of said stylet body.

68. The system of claim 58 wherein said second end of said lower hollow portion terminates in an open configuration.

69. The system of claim 58 wherein said second end of said lower hollow portion terminates in a generally closed configuration and wherein said second end of said lower hollow portion includes at least one hole to permit the passage of fluid into and out of said lower hollow portion.

70. The system of claim 58 wherein the ultimate end of said second end of said lower hollow portion is generally rounded.

\* \* \* \* \*

UNITED STATES PATENT AND TRADEMARK OFFICE
CERTIFICATE OF CORRECTION

PATENT NO. : 5,603,703
DATED      : February 18, 1997
INVENTOR(S): Elsberry et al.

It is certified that error appears in the above-indentified patent and that said Letters Patent is hereby corrected as shown below:

Col. 9, Line 53:   "styler" should be "stylet"

Col. 1, Line 4:    "present" should be "The present"

Col. 1, Line 5:    "styler" should be "stylet"

Signed and Sealed this

Twenty-third Day of September, 1997

*Attest:*

BRUCE LEHMAN

*Attesting Officer*    Commissioner of Patents and Trademarks